United States Patent [19]

Meunier

[11] 4,258,135
[45] Mar. 24, 1981

[54] DEVICE FOR USE IN THE STUDY OF BIOCHEMICAL OR ENZYMATIC REACTIONS

[76] Inventor: Henry E. Meunier, 24 avenue Alsace Lorraine, 38000 Grenoble, France

[21] Appl. No.: 40,906

[22] Filed: May 21, 1979

Related U.S. Application Data

[63] Continuation-in-part of Ser. No. 955,921, Oct. 30, 1978.

[51] Int. Cl.³ .............................................. C12M 1/20
[52] U.S. Cl. ..................... 435/301; 141/31; 422/61; 435/30; 435/810
[58] Field of Search ................... 435/30, 32, 33, 34, 435/40, 287, 296, 297, 298, 299, 300, 301, 317; 422/55, 58, 61; 141/31, 34

[56] References Cited

U.S. PATENT DOCUMENTS

| | | | |
|---|---|---|---|
| 3,367,841 | 2/1968 | Buissiere et al. | 435/34 |
| 3,690,836 | 9/1972 | Buissiere et al. | 435/291 X |
| 3,694,320 | 9/1972 | Buissiere | 435/34 X |
| 3,986,534 | 10/1976 | Schmidt | 435/296 X |
| 4,070,248 | 1/1978 | Schmidt | 435/30 X |

*Primary Examiner*—Robert J. Warden
*Attorney, Agent, or Firm*—Gordon W. Hueschen

[57] ABSTRACT

An improved device for the study of biochemical or enzymatic reactions produced by living organisms is disclosed. The device comprises a sandwich of two plastic sheets sealed to each other, the said sandwich having a central open area with upstanding walls which define a central receptacle which is closed at its bottom by one of said plastic sheets. Internal of the sandwich are a plurality of radially-extending cavities providing individual reaction chambers, which are in communication with the central receptacle internal of the sandwich, as by means of capillaries of reduced cross-section with respect to the reaction chambers themselves. The reaction chambers have apertures therein, preferably at their radially-outwardly extending portions, to enable aerobic growth therein. The device also comprises a central cap which fits down snugly internal of the central receptacle and the walls of which correspond to the inside of the walls of the central receptacle and are preferably of a height which enables the cap to extend to the bottom thereof, thereby isolating whatever is in the reaction chambers from the central receptacle.

The central cap is structured and positioned, preferably within said central receptacle, so as to constitute a plunger or piston and create a plunger or piston effect upon being pushed downwardly within the corresponding "cylinder bore" of said central receptacle, thereby to distribute the sample into the individual reaction chambers.

26 Claims, 9 Drawing Figures

DEVICE FOR USE IN THE STUDY OF BIOCHEMICAL OR ENZYMATIC REACTIONS

The present application is a Continuation-In-Part of my prior-file copending application Ser. No. 955,921, filed Oct. 30, 1978, in which a Notice of Allowance has been received under date of Apr. 2, 1980.

BACKGROUND OF INVENTION

1. Field of Invention

The present invention relates to a device which is of particular utility in laboratories for the study of chemical or biological reactions and particularly biochemical or enzymatic reactions produced by living organisms, particularly microorganisms, in the form of patient samples, cell suspensions, or the like. The invention is more particularly concerned with an improved device of the type described whereby, for example, cell suspensions may be introduced into a central receptacle, the cell suspensions distributed into reaction chambers by centrifugation or by a plunger or piston effect, and the metabolic utilization of chemicals or substrata by such cells or enzymes produced thereby may be observed by observing changes, e.g., density, turbidity, or color changes, within the individual reaction chambers of the device.

2. Prior Art

Devices of this kind are known in the art, but suffer from numerous disadvantages, among which may be mentioned particularly inconvenience and excessive labor, as well as possible variation between samples or sample contamination, all due to the inherent limitations of devices as previously provided. Among such devices having such inherent defects may be mentioned the devices of prior U.S. Pat. Nos. 3,367,841, 3,694,320, and 3,690,836, with respect to all of which the device of the present invention presents a most substantial improvement.

OBJECTS OF THE INVENTION

It is an object of the present invention to provide an improved test device for the study of biochemical or enzymatic reactions produced by living organisms or in general for the study of chemical or biological reactions, as desired. It is a further object of the invention to provide such a device which is economical to manufacture, accurate, readily utilizable, and which substantially reduces the inconvenience, excess labor, and chance of error involved with previous devices of generally the same type when utilized for generally the same purpose. Additional objects of the invention are to avoid the disadvantages of the prior art and to obtain such advantages as will appear hereinafter. Still further objects of the invention will be apparent to one skilled in the art as the description proceeds.

BRIEF DESCRIPTION OF THE INVENTION

The invention comprises an improved device for the study of biochemical or enzymatic reactions produced by living organisms. The device comprises a sandwich of two plastic sheets sealed to each other, the said sandwich having a central open area with upstanding walls which define a central receptacle which is closed at its bottom by one of said plastic sheets. Internal of the sandwich are a plurality of radially-extending cavities providing individual reaction chambers, which are in communication with the central receptacle internal of the sandwich, as by means of capillaries of reduced cross-section with respect to the reaction chambers themselves. The reaction chambers have apertures therein, preferably at their radially-outwardly extending portions, to enable aerobic growth therein. The reaction chambers may be provided with sheets of absorbent material and/or color-producing reagents, which are preferably in said absorbent material. The device may also be provided with means such as indentations for positioning of the device on the axis of a horizontal centrifuge, so that samples may be placed therein through the central receptacle portion and readily distributed into the individual reaction chambers thereof by means of rotation on a standard centrifuge. The device also preferably comprises a central cap which fits down snugly, preferably interally, of the central receptacle and the walls of which correspond to the inside of the walls of the central receptacle and are preferably of a height which enables the cap to extend to the bottom thereof, thereby isolating whatever is in the reaction chambers from the central receptacle. The entire device, before or after distribution of the sample into the individual reaction chambers, may have the central cap placed therein and in turn be placed into a Petri dish or similar incubation vessel, preferably provided with a layer of absorbent material therein to provide necessary moisture, and incubated in usual manner to produce reactions and/or color reactions in the various reaction chambers for purposes of characterizing or identifying the specimen placed in the central receptacle for testing. Alternatively, a snugly-fitting central cap having its walls fitting snugly internal or external of the walls of the central receptacle, and corresponding closely thereto, can be employed to create a "plunger" or "piston" effect, and by a downward push, after the cell suspension or the like has been placed into the central receptacle, utilized to distribute the sample by a single stroke into the individual reaction chambers in the same manner as though centrifugation had taken place. This of course eliminates the necessity of centrifugation, and involves a much simpler manipulative procedure. After distribution of the sample into the reaction chambers, the procedure is of course identical to that described in the foregoing.

BRIEF DESCRIPTION OF THE DRAWINGS

The invention in its preferred embodiment is illustrated by, and may be more readily understood from, the accompanying Drawings, in which.

DESCRIPTION OF THE PREFERRED EMBODIMENTS

Figure 1:
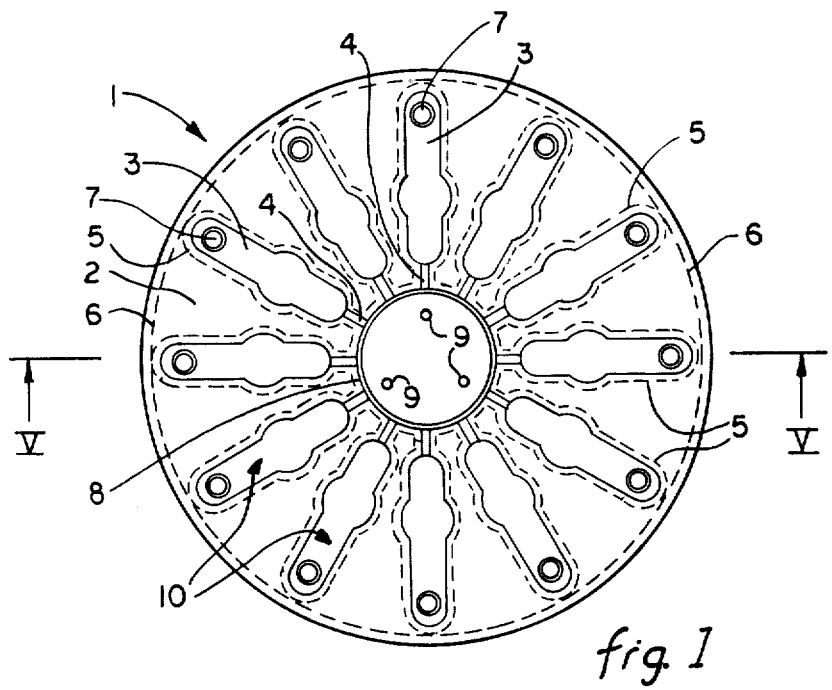
FIG. 1 is a top plan view showing a device in accord with the present invention.
Figure 2:
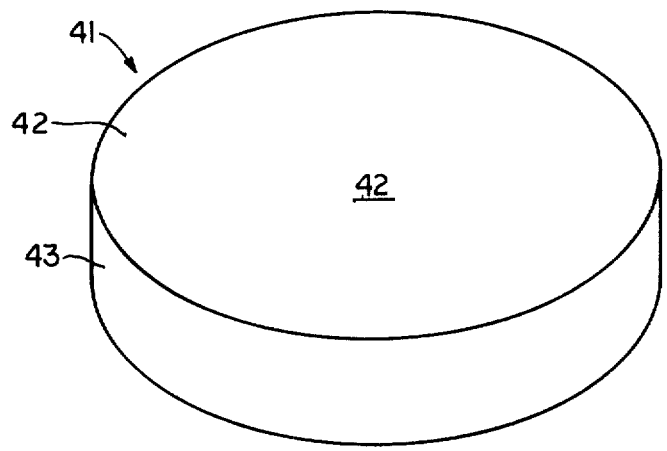
FIG. 2 is an exploded perspective view showing in super position the various elements which cooperate to form the structure of the device according to FIG. 1.
Figure 2:
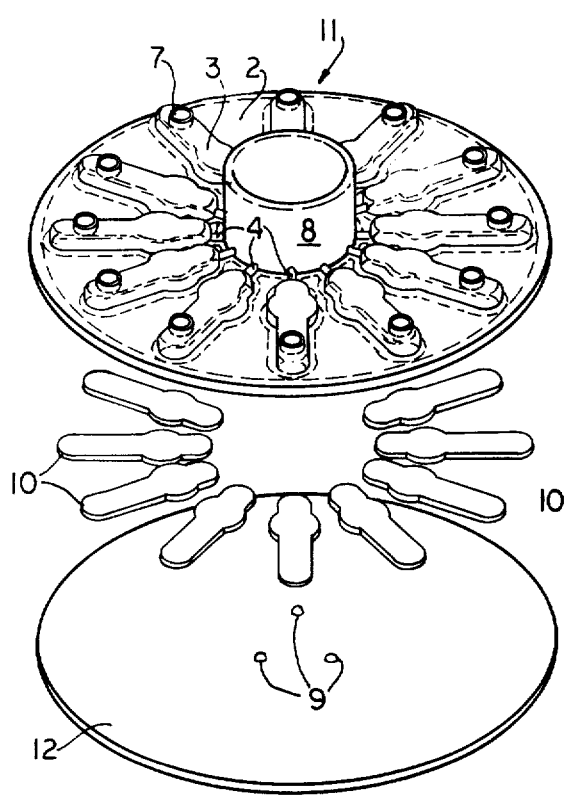

Referring now particularly to FIGS. 1 and 2, the device generally is shown in top plan view at 1 and in an exploded perspective view showing all the elements of the device at 11. The elements of the device shown at 11 are shown in the form of a compressed and integral sandwich at 1. The sandwich of the device comprises two plastic sheets, an upper sheet 2 and a lower sheet 12, the lower sheet of which is substantially planar in nature except for elements 9 therein, which will be further described hereinafter. The first or top sheet 2 is dimensioned and contoured with upstanding walls 8 so as to provide a central receptacle in sheet 2. Internal of the sandwich are provided radially-extending cavities defining individual reaction chambers 3, each of which is connected to the bottom of the central receptacle by means of channels or capillaries 4. As shown, these individual reaction chambers 3 and connecting channels or capillaries 4 are most advantageously formed in a single one of the two plastic sheets, here in the first or upper sheet 2, but a portion of said reaction chambers and capillaries 4 may of course extend into or be provided in the second or lower sheet 12. In each of the reaction chambers 3, preferably at their radially outwardly-extending portions, is provided an aperture 7, as shown in FIGS. 1 and 2 having upwardly-extending walls in this case in the form of upwardly-turned edges of said apertures, to prevent spillage of contents from within reaction chambers 3 upon utilization of the device of the invention, especially when spun upon a horizontal centrifuge (not shown). The individual reaction chambers are conveniently provided by the radially-extending cavities in one or more of sheets 2 and 12, and are conveniently defined by sealing sheets 2 and 12 to each other along the edges of the individual reaction chambers by adhesive, heat-sealing, or other means. The two plastic sheets 2 and 12 constituting the outer layers of the sandwich are also advantageously sealed to each other in the same manner along the edges of the capillaries connecting the central receptacle and the reaction chambers 3, the high-frequency weld lines being shown at 5. The two plastic sheets 2 and 12 comprising the sandwich are also conveniently and advantageously sealed to each other along their outer edges, where the high-frequency weld line is shown at 6. Elements 9 in the bottom sheet 12 are, as shown, indentations providing means for positioning the device on the axis of a horizontal centrifuge (having corresponding protuberances) after introduction of the specimen to be tested into the central receptacle defined in the device by upstanding walls 8. Alternative means for positioning the device on the axis of a horizontal centrifuge may be studs, points, spurs, or any other structure convenient for the said purpose. Elements 9 are of course optional and may be omitted when it is not intended that the device shall be utilized by spinning upon a horizontal centrifuge, for example, in case it is to be employed by utilizing the central cap 31 and its "plunger" or "piston" effect for distribution of the specimen by a single downward stroke into the individual reaction chambers 3.

Within the individual reaction chambers 3 are preferably located sheets of absorbent material, as shown at 10, shaped so as to fit individually within the individual reaction chambers 3. Such absorbent materials generally also contain, by impregnation or on the surface thereof, a color-producing reagent, and the individual reaction chambers generally contain different color-producing reagents, so as to provide each individual reaction chamber with an individual color-producing reagent to indicate, characterize, or identify the material in the specimen placed into the central receptacle, either by reaction directly of the sample or a microorganism in said sample or an enzyme in or produced in said sample with the color reagent, or indirectly with another chemical in the reaction chamber which in turn produces a known color reaction, all as well known in the art. Such chemicals and/or color-producing reagents can be distributed on the surface of the absorbent material 10 or the absorbent material 10 may have the same impregnated thereinto. Alternatively, as is also well known in the art, the absorbent material may in some cases be dispensed with entirely and the chemical and/or color-producing reagent supplied directly on the surface of reaction chamber 3 as by coatng thereon or placement thereinto, again as is well known in the art.

Figure 3:
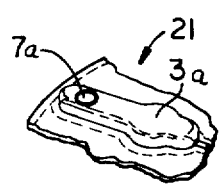
FIG. 3 is a fragmentary breakout of FIG. 2 showing a modification of the invention illustrated in FIG. 1.

FIG. 3 shows at 21 a fragmentary breakout from FIG. 2 illustrating a modification of the invention wherein the reaction chamber 3a is substantially identical to reaction chamber 3, but wherein aperture 7a does not have the upwardly-turned edges. Such structure is satisfactory but is not recommended in cases where the device is to be charged with considerable test material or employed upon a high speed centrifuge, since, in such cases, content of reaction chamber 3a is likely to escape through aperture 7a with attendant inconvenience and disadvantage.

Figure 4:
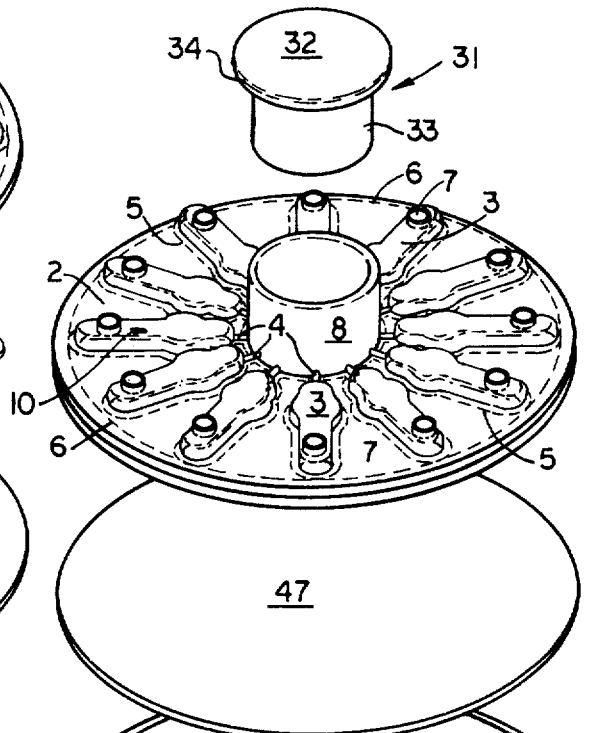
FIG. 4 is an exploded perspective view of a final test assembly as utilized in practice showing in superposition the various elements which cooperate to form the final assembly, and in which the device illustrated in exploded perspective view in FIG. 2 is shown in assembled condition.
Figure 4:
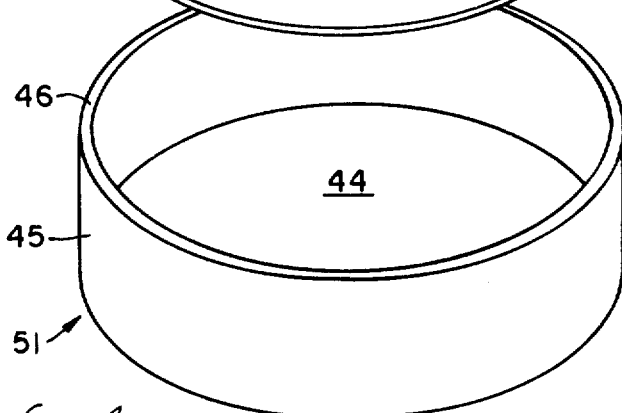

Turning now to FIG. 4, the device of FIG. 2 is again shown fully assembled as in FIG. 1, but this time as part of a final assembly as utilized in practice. Shown in superposition at 31 is a central cap comprising a top portion 32 with suitable overhanging flange at 34 and vertical walls 33. This cap is designed so that its walls 33 correspond to the outside or inside, preferably the inside, of the walls 8 of the central receptacle, thereby to constitute the cap and central receptacle approximately as piston and cylinder bore respectively, and the said walls 33 are preferably of a height which enables said cap to extend to the bottom of the central receptacle of the device, thereby to isolate whatever is in said reaction chambers 3, by virtue of having been placed into said central receptacle, from said central receptacle, after centrifugation—or distribution into chambers 3 through channels or capillaries 4 by other means, as by utilizing the "plunger" or "piston" effect of central cap 31, as will be further described hereinafter. The walls 33 of cap 31 should, therefore, ordinarily and preferably, but not necessarily, be of greater height than the veritcal height of walls 8 of the central receptacle of the device.

Also shown in FIG. 4, in addition to the device itself and its complementary cap, are the other usual elements of a Petri dish, the familiar microbiological and bacteriological tool. Shown at 41 is the Petri dish cover and at 51 the Petri dish itself, the cover comprising top 42 with downwardly-extending vertical walls 43, designed to fit over the outside of the corresponding vertically-extending walls 45 of the Petri dish 51, having its own horizontal bottom 44 complementary to horizontal top 42 of the Petri dish cover 41, and rest upon rim 46. Also shown is a further sheet of absorbent material 47, such as the usual porous blotting paper or the like, which may advantageously be impregnated with water to provide suitable atmospheric moisture during incubation of the total assembly as will be described hereinafter.

Figure 5:
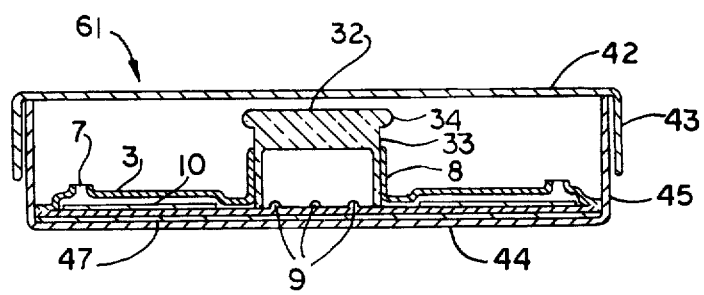
FIG. 5 is a diagrammatic transverse section of the device of the invention along lines V—V of FIG. 1 in place in a final assembly as utilized in practice and including all of the elements of the final assembly as illustrated in FIG. 4.

The total assembly is shown in FIG. 5, in which the device of the invention is shown in a diagrammatic transverse section along lines V—V of FIG. 1. All of the various previously-mentioned elements are seen in this cross-sectional view, the test device of the invention being in place with its complementary cap likewise in place therein and, as shown, cutting off the central receptacle from the radially-extending reaction chambers by virtue of the fact that the walls 33 thereof are of greater height than the height of the walls 8 of the central receptacle as formed in first or upper plastic sheet 2. The device of the invention is shown superposed upon absorbent sheet 47 within the Petri dish, the cover 41 of which is now in place over the Petri dish 51. As shown at 61, the entire assembly is ready for placement in an incubator, assuming that the specimen for analysis has previously been placed into the central receptacle defined by upstanding walls 8 and centrifuged or otherwise forced outwardly into the individual reaction chambers 3. As seen, it should be clear that the device of the present invention is preferably essentially circular, as is the central receptacle therein, for maximum convenience, but that it or its central receptacle could also take numerous other shapes if so desired or if convenient for any intended purpose. As shown, the central receptacle has a volume which is at least as great as the total volume of all the reaction chambers present in the device, and in fact it is preferred that the central receptacle have a volume which is greater than the total volume of all the reaction chambers present in the device, but such is not essential except for convenience and for distribution of the test specimen throughout all of the test chambers provided during the centrifugation step or other distribution step employed in its utilization.

Also, although the device as shown has twelve (12) individual reaction chambers, it should be clear that the only limitation is one of size and convenience and there is no reason why up to as many as twenty-four (24) reaction chambers, or even more, cannot be provided in a single device if only space and convenience permit. Likewise, a lesser number of chambers can be provided, although this is not advantageous from the standpoint of economy unless only a few tests are desired to be run upon a single specimen.

In operation, the specimen to be tested, for example, a cell suspension of living organisms, is simply introduced into the central receptacle of the device defined by upstanding walls 8. The device may then be placed upon a suitable horizontal centrifuge, where it is spun and to which it is securely held by securing means 9, indentations which correspond to protuberances (not shown) at the axis of the horizontal centrifuge employed (also not shown). The material to be tested spreads outwardly during centrifugation through capillaries 4 and into the various reaction chambers 3, where it is distributed evenly, the speed of the centrifuge and the length of time the device is spun on the centrifuge being predetermined. The complementary cap 31 is then put in place within upstanding walls 8 of the central receptacle, thereby preferably cutting off the communication between the radially-extending reaction chambers 3 and the bottom of the central receptacle.

Alternatively, the complementary cap 31 may be put in place immediately after the specimen to be tested is introduced into the central receptacle defined by upstanding walls 8. Due to the snug fit of the walls of central cap 31 complementary to the upstanding walls 8 of the central receptacle, pressure may then be applied to the complementary cap to effect a downward stroke thereof, thereby producing a so-called "plunger" or "piston" effect, the result of which is the outward spreading of the test sample under pressure through the capillaries 4 and into the various reaction chambers 3, where it is distributed evenly in the same manner as though centrifugation had been employed, but by means of a much simpler and less time-consuming manipulative step. In either case, the sample is at this point evenly distributed in the various reaction chambers 3, and ready for further processing.

The device is then placed within a Petri dish or similar receptacle, advantageously containing a moistened sheet of blotting paper on the bottom thereof, the cover placed thereupon, and the entire assembly incubated for the selected time period in order to permit the test material to grow and reproduce, if a living organism, and/or otherwise to react either with color-forming reagents within reaction chambers 3 or with other chemicals designed to give, with the test material or with an enzyme or other product of the growth thereof, a further product which in turn will produce a color reaction with the color-producing reagent, all as is well known to one skilled in the art. After the desired period of incubation, the device can be examined for color changes in the various reaction chambers thereof and the results compared with known color changes produced by known specimens or samples, thereby to characterize or identify the test specimen or a a major component thereof. It goes without saying that the individual reaction chambers may also contain suitable growth media, either instead of or in addition to other chemicals and/or color-forming reagents, to facilitate growth of microorganisms in the test specimen, if desired.

As will be readily apparent to one skilled in the art, the device of the invention can be used to study biochemical or enzymatic reactions produced by all kinds of living organisms, such as bacteria, yeasts, and the like, in contact with various reagents, substrates, antibiotics, or the like, or it can in fact be used merely to test different chemical entities for their particular reaction with different reagents, in each of which cases the color-producing reagent, when present within the individual reaction chambers, will be selected according to the purpose of the test and the material for which the test is designed.

The new device of the invention obviously may be employed to great advantage inasmuch as it saves a great deal of time and simplifies manipulations greatly as compared to all other previously known or described devices for the same purpose, for instance, those of the reference patents mentioned.

As is well known in the art, the volume of the individual reaction chambers is preferably predetermined and of a standard value, although their exact shape is not of great significance and can vary widely. As well known in the art also, the sheet of absorbent paper or other porous material within the individual reaction chambers may bear, carry, or be impregnated with the reagent, a substrate, an antibody, or so on, in convenient quantity for carrying out the particular test involved. The absorbent paper, when present, may be either in the form of a disc, a sheet cut to the dimensions of the individual reaction chamber itself, in the form of a single such disc or two discs, in either horizontal or vertical juxtaposition, each of which may be impregnated with a different reagent, or, as a further alternative, no absorbent material at all may be present in the individual reaction chambers, in which case the medium or reagent may be coated on or present in the individual reaction chamber itself, as by being coated in a thin dried-out layer directly upon the plastic surface of the reaction chamber instead of being impregnated or coated within or onto the absorbent material and then dried.

It will also be apparent to one skilled in the art that there will always be two different zones within the individual reaction chambers, namely, an aerobic zone around the aperture 7 or 7a and an anaerobic zone elsewhere within the reaction chamber. The aperture also allows air to escape while the device is in place spinning upon a centrifuge, or while the test sample is otherwise being distributed to the reaction chambers, thus allowing the organism suspension or other test material placed into the central receptacle to be forced by centrifugation and/or centrifugal or other force, e.g., the piston or plunger force heretofore referred to, through the capillaries 4 into the individual reaction chambers 3 until they are substantially filled with test material. The upstanding wall of the aperture 7 is, as previously stated, for purposes of maintaining test material within the individual reaction chambers when it is desired or convenient or necessary to fill them with substantial quantities of the organism suspension or other material to be tested. A clear advantage of the simplicity of the system here described is that a measured quantity of the living organism suspension or other test material is merely introduced into the central receptacle, the device indexed and adjusted upon a small laboratory centrifuge, spun for a predetermined short period of time, during which all the tubes are filled similarly and simultaneously, removed from the centrifuge, and subjected to incubation as previously described for a predetermined period, after which the necessary reading may be taken.

When the "plunger" or "piston" effect of the snugly-fitting central cap 31, having walls which are complementary with and in extremely tight-fitting relationship to the upstanding walls 8 of the central cavity, is employed, the procedure and manipulative steps are even further simplified. This "plunger" or "piston" effect is utilized merely by pressing upon the top portion of the central cap to create a single downward stroke, which in turn exerts a pressure upon the specimen already deposited within the central receptacle between the walls 8 thereof. The result is the outward dispersal of the test specimen through the channels or capillaries 4 into the reaction chambers 3, where it is evenly distributed, so that further processing may ensue. It will be clear that the employment of the central cap 31 for purposes of creating this "plunger" or "piston" effect method of distributing the test specimen into the reaction chambers 3 is about as simple and minimally time-consuming a step as can be conceived, eliminating the need for centrifugation if this is considered undesirable for any reason, and allowing the employment of minimal manual labor and maximum time savings in carrying out the necessary steps of preparing a sample for incubation.

With the device of the present invention, it is no longer necessary to fill a large number of holes or test chambers each individually with test material, which is extremely inconvenient, time-consuming, and likely to cause contamination and variation, especially since it is no longer necessary to employ a multiplicity of pipettes or to touch a pipette containing the test material to a plurality of test chamber openings, but rather only to introduce the entire amount of the material to be tested at one time into the central receptacle of the device of the invention. An obvious advantage of the device being circular is that it fits into an ordinary Petri dish, when similarly dimensioned, the only requirement being that in such case the diameter of the circular device be slightly less than that of a standard Petri dish. The sheet of filter paper moistened with water to ensure incubation in a moist atmosphere, suggested previously for placement at the bottom of the Petri dish employed, although not essential, is as usual highly recommended according to the known art of microbiology.

Figure 6:
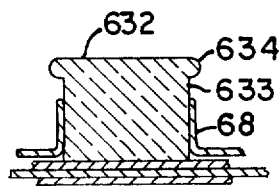
FIG. 6 is a partial diagrammatic transverse section of another embodiment of the device of the invention not particularly adapted for employment on a centrifuge.
Figure 7:
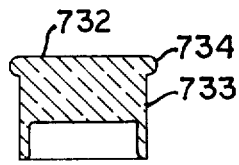
FIG. 7 is a transverse section of another form of the central cap.
Figure 8:
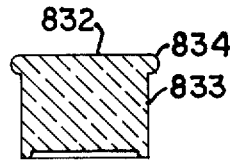
FIG. 8 is a transverse section of a further form of the central cap.
Figure 9:
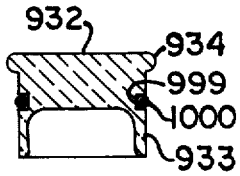
FIG. 9 is a transverse section of still another form of the central cap, in this case including a sealing ring.

Alternative structures which may be employed for the central cap are shown in transverse section in FIGS. 6 through 9. In FIG. 6, the partial transverse section includes upstanding walls 68 of the central cavity, as well as top portion 632, flange 634, and vertical walls 633. In the embodiment of FIG. 7, the central cap is shown having a greater solid portion than in FIG. 5, but a lesser solid portion than as shown in FIG. 6. The respective top portion, flange, and vertical walls are designated 732, 734, and 733 in FIG. 7. In FIG. 8, the central cap embodiment shown has a lesser solid portion than the embodiment of FIG. 6 and a greater solid portion than the embodiment shown in FIG. 7. The top portion, vertical walls, and flange are respectively numbered 832, 833, and 834 in FIG. 8. The embodiment of FIG. 9 is provided with an internal cavity approximately equal to that of the embodiment of FIG. 7, but of different contour, and the top portion, vertical walls, and flange are respectively designated 932, 933, and 934 in FIG. 9. In addition, the embodiment of FIG. 9 is provided with a sealing O-ring 1000 of rubber, plastic, elastomer, or of other resilient but impervious material, so as to ensure a substantially airtight seal between the upstanding walls 8 of the central receptacle and the vertical walls 933 of the central cap embodiment of FIG. 9. As shown, the sealing O-ring 1000 may conveniently be seated in an indentation or recess in vertical walls 933 identified in FIG. 9 as 999. The advantages of the device of the present invention are maximized when employing the "plunger" or "piston" previously referred to but, even when centrifugation is the mode of choice for distribution of the specimen into the various reaction containers of the device of the invention, its advantages over any and all known prior art devices is readily apparent. When a sealing ring of the nature of 1000 in FIG. 9 is employed, it goes without saying that it should preferably be sterile, the same as other components of the device of the invention, to avoid undesirable contamination and consequent incorrect readings or results.

A most convenient feature of employing the device of the present invention, in the case where an absorbent material is present in the individual reaction chambers thereof, or when the bottom plastic sheet is white or of light color, is that one can read a color reaction directly through the transparent wall of the reaction chamber as provided by the first or upper plastic sheet 2.

On the other hand, if the individual reaction chambers do not contain absorbent material and if both of the two plastic sheets constituting the device of the present invention are of clear plastic of known optical density, it is a simple matter to measure by nephelometry a change of turbidity in the suspension involved. This increase or change of turbidity in the cell suspension or other material being tested is of particular interest if it is desired to employ the device for measuring the MIC (minimal inhibitory concentration) of one material against another, e.g., an antibiotic against a germ, this being an essential feature of antibiotic sensitivity testing by the dilution method. The nephelometric measurement can, in such cases when desired, be made simply by employing an automatic electronic device.

As already mentioned, the ordinary and most simple manner of producing a device according to the present invention is by employing two preformed sheets of plastic and sealing them together by adhesive, heat, ultrasonically, or in any other way. In such case, any absorbent material desired to be present within the reaction chambers of the device can be impregnated, dried, cut before sealing, and placed within the preformed cavities before sealing, with an automatic device. Alternatively, when impregnation is desired after sealing, by techniques which are well established in the art and as disclosed, for example in U.S. Pat. No. 3,690,836, namely, by introducing the desired color-producing reagent or other indicating reagent, alone or together with any other desired or necessary chemical for the production of the desired color reaction upon contact with the necessary test material or an enzyme or other metabolite thereof, directly into the reaction chamber and into any absorbent material present therein through the aperture 7 or 7a thereof.

It will be understood that within the reaction chamber of preferably given volume, but the shape of which may vary infinitely, there may be either a sheet of paper or other absorbent material, impregnated or intended to be impregnated, with suitable reagents in suitable quantity , or a disc of paper or other absorbent material, illustratively only in a bulged central portion of the reaction chamber of the device, which may or may not be impregnated before being placed into position within the chamber with suitable reagents in suitable quantity, or that two sheets or discs of paper or other absorbent material, either superposed or adjacent, and either containing or intended to contain different suitable reagents in different suitable quantities, or no absorbent element whatever, may be present therein, in which latter case the reagents may then be put in place within the chamber either in dry condition or in solution or suspension and then dried in place by evaporation or freeze drying of a solution, said putting in place being either prior to or after formation of the sandwich of the present invention according to either of the procedures indicated previously.

Although the sandwich of the invention may be united by adhesive, heat, heat welding, or ultrasonics, in a step-wise manner, it is to be understood that it can also be conveniently prepared in a single step by simultaneous welding and shaping of two plastic sheets or plates, separated or not by one or a plurality of absorbent elements, with welding and shaping being effected simultaneously, for instance, by a high-frequency electrode of a suitable shape and size. The exact manner of preparation of the device according to the present invention is of course immaterial.

As already stated, the device and system of the present invention provide the advantage of permitting an appreciable reduction in the time necessary for carrying out tests employing devices presently available for the same type of test procedure. It is of course sufficient merely to deposit a suitable quantity of cell suspension of a germ to be studied, or the like, within the central receptacle of the device of the invention, and thereafter to place the unit on a suitable centrifuge, the index or fastening system assuring suitable positioning thereon. By turning the centrifuge at a given rate of speed for a suitable time period, the individual reaction chambers will be filled simultaneously and accurately, the liquid of the cell suspension or the like being forced outwardly by centrifugal force through the capillaries and into the individual reaction chambers of the device of the invention, while air therein is exhausted through the exhaust apertures provided at the outer ends of the said individual reaction chambers. As previously explained, when using the "plunger" or "piston" effect of the tightly-fitting central cap, the individual reaction chambers can be filled simultaneously and accurately by merely employing a single downward stroke of the central cap, the walls of which are in close-fitting and essentially airtight contact with the upstanding walls 8 of the central receptacle, thereby to create an instantaneous internal pressure for subjecting the liquid, of the cell suspension or the like undergoing the test, to an outward pressure or force, through the capillaries and into the individual reaction chambers, again with the exhaustion of air through the exhaust apertures provided in the individual reaction chambers, preferably at the outer ends thereof, with the walls of the central cap and the walls of the central receptacle in close-fitting relationship, establishing the relationship between the cap and receptacle walls of piston and cylinder bore, respectively. The desired "plunger" or "piston" effect is conveniently accomplished by a single downward stroke of the "piston". The necessary piston displacement, that is, the volume of air displaced by a single downward stroke of the "piston", i.e., the central cap, being a function of the downward travel distance of the "piston" and the cross-sectional area of the containing cylinder, i.e., the central receptacle, is readily attainable so as to cause sufficient pressure for outward distribution of the test specimen, and is moreover fully within the skill of the art.

It is of course to be understood that examples of the study devices disclosed and claimed herein and capable of being provided according to the present invention could be greatly multiplied. It is conceived in particular that the planned profile of the devices, as well as the number of perforations and apertures and individual reaction chambers and capillaries leading thereto from the central receptacle, may be varied practically without limit, as may other aspects of the structure of the device of the present invention, for which reason it is to be understood that the invention is not limited to the exact details of construction, operation, or exact materials or embodiments shown and described, as obvious modifications and equivalents will be apparent to one skilled in the art, and the invention is therefore to be limited only by the full scope of the appended claims.

I claim:

1. A device for the study of biochemical or enzymatic reactions produced by living organisms, comprising a sandwich of two plastic sheets sealed to each other, the first sheet of said sandwich being dimensioned and contoured so as to provide a central open area having upstanding walls, defining a central receptacle, said central receptacle being closed at its bottom by the second of said sheets, the said sandwich having internal thereof a plurality of radially-extending cavities providing individual reaction chambers, said reaction chambers having exhaust apertures therein, said reaction chambers being in communication with said central receptacle internal of said sandwich, said device comprising also a central cap, having walls corresponding to the walls of said central receptacle, the said walls of central cap corresponding to the walls of said central receptacle in close-fitting and essentially airtight relationship so as to establish the relationship of a piston and cylinder bore and enable creation of a pressure within said central receptacle upon said central cap being pushed downwardly.

2. The device of claim 1, wherein said chambers are in communication with said central receptacle by means of further cavities providing capillaries of reduced cross-section with respect to said reaction chambers arranged between said reaction chambers and said central receptacle and providing communication between the bottom of said central receptacle and said radially-extending reaction chambers.

3. The device of claim 2, wherein said second sheet is substantially flat and cavities are provided in said first sheet.

4. The device of claim 3, wherein said capillaries are provided in the form of channels in said first sheet.

5. The device of claim 1, wherein said apertures are so formed in said reaction chambers as to have upwardly-extending walls.

6. The device of claim 5, wherein said upwardly-extending walls are in the form of upwardly-turned edges of said apertures.

7. The device of claim 1, wherein the exhaust apertures are present in said reaction chambers at the radially outwardly-extending portions of said reaction chambers.

8. The device of claim 1, wherein the central receptacle has a volume which is at least as great as the total volume of all the reaction chambers present in the device.

9. The device of claim 8, wherein the central receptacle has a volume which is greater than the total volume of all the reaction chambers present in the device.

10. The device of claim 1, wherein the two plastic sheets constituting the elements of the sandwich are sealed to each other along the edges of the individual reaction chambers.

11. The device of claim 10, wherein the two plastic sheets are also sealed to each other along the edges of the capillaries connecting the central receptacle and reaction chambers.

12. The device of claim 10, wherein the two plastic sheets comprising the sandwich are also sealed to each other along their outer edges.

13. The device of claim 1, wherein means is provided in said second plastic sheet for positioning of the device on the axis of a horizontal centrifuge.

14. The device of claim 13, wherein said means constitutes studs, points, spurs, or indentations.

15. The device of claim 1, comprising sheets of absorbent material within the individual reaction chambers.

16. The device of claim 15, wherein said absorbent sheets are shaped so as to fit individually within the individual reaction chambers.

17. The device of claim 1, wherein the reaction chambers contain a color-producing reagent.

18. The device of claim 17, wherein the different reaction chambers contain different color-producing reagents.

19. The device of claim 18, wherein the color-producing reagents are in or on said absorbent material.

20. The device of claim 1, wherein the walls of the central cap correspond to the inside of the walls of said central receptacle and are of a height enabling said cap to extend to the bottom of said central receptacle, thereby to isolate said reaction chambers from said central receptacle.

21. The device of claim 1, wherein said pressure internal of said central receptacle created by the downward movement of said central cap within said central receptacle is sufficient to distribute test material deposited within said central receptacle substantially evenly within said individual reaction chambers.

22. The device of claim 21, wherein said central cap is fitted with a peripheral sealing ring for purposes of effecting a close-fitting and essentially airtight relationship between the walls of said central cap and said central receptacle.

23. The device of claim 1, including said central cap, in a Petri dish with the cover of the Petri dish superimposed in normal position over the bottom of said Petri dish.

24. The device of claim 23, wherein said sandwich and the central receptacle thereof are both essentially circular in top plan view.

25. The device of claim 23, including a sheet of absorbent material between said device and the bottom of said Petri dish.

26. The device of claim 1, wherein said sandwich and the central receptacle thereof are both essentially circular in top plan view.

* * * * *